(12) United States Patent
Song et al.

(10) Patent No.: US 6,376,240 B1
(45) Date of Patent: Apr. 23, 2002

(54) RFLAT-1: A TRANSCRIPTION FACTOR THAT ACTIVATES RANTES GENE EXPRESSION

(75) Inventors: An M. Song; Ya-Fen Chen; Alan M. Krensky, all of Stanford, CA (US)

(73) Assignee: Board of Trustees of the Leland Stanford Junior Unversity, Palo Alto, CA (US)

( * ) Notice: Subject to any disclaimer, the term of this patent is extended or adjusted under 35 U.S.C. 154(b) by 0 days.

(21) Appl. No.: 09/492,985

(22) Filed: Jan. 27, 2000

Related U.S. Application Data
(60) Provisional application No. 60/117,576, filed on Jan. 27, 1999.

(51) Int. Cl.[7] .............................. C12N 1/21; C12N 5/00; C12N 15/00; C12N 15/09; C07H 21/04
(52) U.S. Cl. .................... 435/325; 435/252.3; 435/410; 435/69.1; 435/320.1; 536/23.1; 536/23.5
(58) Field of Search .................. 536/23.1, 23.5; 435/325, 252.2, 252.3, 69.1, 410, 320.1

(56) References Cited

U.S. PATENT DOCUMENTS

| | | | |
|---|---|---|---|
| 5,652,133 A | 7/1997 | Murphy | 435/325 |
| 5,707,814 A | 1/1998 | Levy et al. | 435/7.1 |
| 5,840,544 A | 11/1998 | Hawkins et al. | 435/69.5 |

FOREIGN PATENT DOCUMENTS

| | | |
|---|---|---|
| WO | 97/00266 | 1/1997 |

OTHER PUBLICATIONS

Berendsen, H.J.C. Science. vol. 282, pp. 642–643, Oct. 1998.*
The 1991 Sigma Catalog, p. 1705, 1991.*

Nelson et al. (1996). "Identification of a novel regulatory region critical fro expression of the RANTES chemokine in activated T lymphocytes" *J. Immunology*, vol. 157(3): 1139–1148.

Oritz et al. (1997). "Switching gears during T–cell maturation: RANTES and late transcription" *Immunology Today*, vol. 18(10):469–471.

Song et al. (1999). "A new zinc finger transcription factor that activates RANTES gene expression in Tlymphocytes" *Immunity*, vol. 10(1):93–13.

Watson et al. (1987). *Molecular Biology of the Gene*, 4th Edition, Benjamin Cummings Publishing Company. p. 69.

Baggiolini, Marco, "Chemokines and Luekocyte Traffic," *Nature* (Apr. 1998) vol. 392:565–568.

Nelson, Peter J., et al., "Chemokines, Lymphocytes and Viruses: What Goes Around, Comes Around," *Current Opinion in Immunology* (1998) vol. 10:265–270.

* cited by examiner

*Primary Examiner*—David Guzo
*Assistant Examiner*—Gerald G. Leffers, Jr.
(74) *Attorney, Agent, or Firm*—Bret E. Field; Paula A. Borden; Bozicevic, Field & Francis LLP

(57) ABSTRACT

A novel zinc finger transcription factore (RFLAT-1) and polypeptides related thereto, as well as nucleic acid compositions encoding the same, are provided. The subject polypeptide and nucleic acid compositions find use in a variety of applications, including diagnostic and therapeutic agent screening applications, as well as in treatment therapies. Also provided are methods of treating disease conditions associated with RANTES function, e.g. inflammation, and the like.

6 Claims, 2 Drawing Sheets

FIG. 1

SEQUENCE LISTING

```
<160> NUMBER OF SEQ ID NOS: 11

<210> SEQ ID NO 1
<211> LENGTH: 1430
<212> TYPE: DNA
<213> ORGANISM: homo sapien
<220> FEATURE:
<223> OTHER INFORMATION: synthetic oligonucleotide probe
<223> OTHER INFORMATION: synthetic oligonucleotide probe

<400> SEQUENCE: 1
gaattcgcgg ccgcgtcgac cggcagctgt cccgcctgcc acaatgcgcg gcgaagctgc      60
ggccgcgact tggcgaggtg gtccctaacg ttgccgctcg gcatccttag aaccggccgc     120
ccctgacgcc gcgcggggac cccagtcgcc cgcgcgcccc atgcgctcac tcttcggtgc     180
ccggccgggc cggcgcctcg cagacgcgga gccgcgcggg tgacggcaca ggcggctgcg     240
cgcccagccc agcccagccc agcccgagga gagggcgcgc cgcgcccccg cccccgccc     300
```

```
gctctcccga ggccgtgggt gcggatgcgc ggctgacgac tcgcagcaag agcaccgccg    360
ccggccccag cccgcagcat ggcagccgcc gcctatgtgg accacttcgc cgccgagtgc    420
ctcgtgtcca tgtcgagccg cgcggtcgtg cacgggccgc gggaggggcc ggagtcccgg    480
cccgagggcg cggccgtggc cgccaccccc acgctgcccc gcgtcgagga gcgccgcgac    540
ggtaaggaca gcgcctcgct cttcgtggtg gcgcggatcc tagcggacct caaccagcaa    600
gcgccggcgc ccgccccggc ggagcgcagg gagggcgccg cggcccggaa ggcgaggacc    660
ccctgccgcc tgccgccgcc cgcccccgag cccacctccc ccggcgccga aggcgcggcg    720
gccgcgcccc ccagcccggc gtggagcgag ccggagcccg aggcggggct ggagcccgag    780
cgggagccgg ggcccgcggg gagcggcgag cccggcctca gacaaagggt ccggcggggc    840
cgaagtcgcg ccgacctcga gtccccgcag aggaagcaca agtgccacta cgcgggctgc    900
gagaaagttt acgggaaatc ttcgcacctc aaggcgcacc tgagaactca cacaggtgag    960
aggcccttcg cctgcagctg caggactgc aacaagaagt tcgcgcgctc cgacgagctg   1020
gcgcggcact accgcacaca cacgggcgag aagaagttca gctgccccat ctgcgagaag   1080
cgcttcatgc gcagcgacca cctgaccaag cacgcgcgcc gccacgccaa cttccacccg   1140
ggaatgctgc agcggcgcgg cggggctcg cggaccggct ccctcagcga ctacagccgc   1200
tccgacgcca gcagcccac catcagcccg gccagctcgc cctgagcccg ccacagccat   1260
gagcagccgc tcccacccccc tcgtgagtcc ctggccttc cttttgtaat aagaaagaag   1320
agagagaact tgatgcaaag tccacgaaaa aacaattttt tcacctcagg tgtcaaagta   1380
aatttgttaa aaaaaaaaaa aaacagcgcg tcgtcgtccg cagcgaattc               1430
```

<210> SEQ ID NO 2
<211> LENGTH: 288
<212> TYPE: PRT
<213> ORGANISM: homo sapien

<400> SEQUENCE: 2

```
Met Ala Ala Ala Ala Tyr Val Asp His Phe Ala Ala Glu Cys Leu Val
 1               5                  10                  15

Ser Met Ser Ser Arg Ala Val Val His Gly Pro Arg Glu Gly Pro Glu
                20                  25                  30

Ser Arg Pro Glu Gly Ala Ala Val Ala Ala Thr Pro Thr Leu Pro Arg
            35                  40                  45

Val Glu Glu Arg Arg Asp Gly Lys Asp Ser Ala Ser Leu Phe Val Val
        50                  55                  60

Ala Arg Ile Leu Ala Asp Leu Asn Gln Gln Ala Pro Ala Pro Ala Pro
 65                  70                  75                  80

Ala Glu Arg Arg Glu Gly Ala Ala Ala Arg Lys Ala Arg Thr Pro Cys
                85                  90                  95

Arg Leu Pro Pro Pro Ala Pro Glu Pro Thr Ser Pro Gly Ala Glu Gly
            100                 105                 110

Ala Ala Ala Ala Pro Pro Ser Pro Ala Trp Ser Glu Pro Glu Pro Glu
        115                 120                 125

Ala Gly Leu Glu Pro Glu Arg Gly Pro Gly Pro Ala Gly Ser Gly Glu
    130                 135                 140

Pro Gly Leu Arg Gln Arg Val Arg Arg Gly Arg Ser Arg Ala Asp Leu
145                 150                 155                 160

Glu Ser Pro Gln Arg Lys His Lys Cys His Tyr Ala Gly Cys Glu Lys
                165                 170                 175
```

```
            Val Tyr Gly Lys Ser Ser His Leu Lys Ala His Leu Arg Thr His Thr
                        180                 185                 190

Gly Glu Arg Pro Phe Ala Cys Ser Trp Gln Asp Cys Asn Lys Lys Phe
                    195                 200                 205

Ala Arg Ser Asp Glu Leu Ala Arg His Tyr Arg Thr His Thr Gly Glu
                210                 215                 220

Lys Lys Phe Ser Cys Pro Ile Cys Glu Lys Arg Phe Met Arg Ser Asp
            225                 230                 235                 240

His Leu Thr Lys His Ala Arg Arg His Ala Asn Phe His Pro Gly Met
                            245                 250                 255

Leu Gln Arg Arg Gly Gly Gly Ser Arg Thr Gly Ser Leu Ser Asp Tyr
                        260                 265                 270

Ser Arg Ser Asp Ala Ser Ser Thr Thr Ile Ser Pro Ala Ser Ser Pro
                        275                 280                 285

<210> SEQ ID NO 3
<211> LENGTH: 13
<212> TYPE: DNA
<213> ORGANISM: homo sapien

<400> SEQUENCE: 3
gcccgcagca tgg                                                           13

<210> SEQ ID NO 4
<211> LENGTH: 100
<212> TYPE: DNA
<213> ORGANISM: Artificial Sequence
<220> FEATURE:
<223> OTHER INFORMATION: synthetic oligonucleotide probe

<400> SEQUENCE: 4
gggaattcga attcgctatt ttggaaactc cccttagggc tattttggaa actccccctta       60 gggctatttt ggaaactccc cttaggctcg agctcgaggg                              100

<210> SEQ ID NO 5
<211> LENGTH: 47
<212> TYPE: DNA
<213> ORGANISM: Artificial Sequence
<220> FEATURE:
<223> OTHER INFORMATION: synthetic oligonucleotide probe

<400> SEQUENCE: 5
aattcgctat tttggaaact ccccttaggg gatgccccctc aactgcg                     47

<210> SEQ ID NO 6
<211> LENGTH: 30
<212> TYPE: DNA
<213> ORGANISM: Artificial Sequence
<220> FEATURE:
<223> OTHER INFORMATION: synthetic oligonucleotide probe

<400> SEQUENCE: 6
aattcgttgc tattttggaa actccccttg                                         30

<210> SEQ ID NO 7
<211> LENGTH: 29
<212> TYPE: DNA
<213> ORGANISM: Artificial Sequence
<220> FEATURE:
<223> OTHER INFORMATION: synthetic oligonucleotide probe

<400> SEQUENCE: 7
```

```
aattcgctag gggatgcccc tcaactgcg                                          29
```

<210> SEQ ID NO 8
<211> LENGTH: 31
<212> TYPE: DNA
<213> ORGANISM: Artificial Sequence
<220> FEATURE:
<223> OTHER INFORMATION: synthetic oligonucleotide probe

<400> SEQUENCE: 8

```
aattctttgt gcaatttcac ttatgatacc g                                       31
```

<210> SEQ ID NO 9
<211> LENGTH: 35
<212> TYPE: DNA
<213> ORGANISM: Artificial Sequence
<220> FEATURE:
<223> OTHER INFORMATION: synthetic oligonucleotide probe

<400> SEQUENCE: 9

```
aattctctag atgagagagc agtgagggag agacg                                   35
```

<210> SEQ ID NO 10
<211> LENGTH: 27
<212> TYPE: DNA
<213> ORGANISM: Artificial Sequence
<220> FEATURE:
<223> OTHER INFORMATION: synthetic oligonucleotide probe

<400> SEQUENCE: 10

```
aattcgtcag agggactttt ccgagag                                            27
```

<210> SEQ ID NO 11
<211> LENGTH: 1471
<212> TYPE: DNA
<213> ORGANISM: mouse

<400> SEQUENCE: 11

```
tggagctcca ccgcggtggc ggccgctcta gactgcagac tagtggatcc ctcgagctac        60
gtcaggggcg accacaactt gcaggggtcg tgcctaacgt cgcctccgct cgacgtccct       120
aagacaggcc gactctgacg ccgcacgcgg accctcctta ctggagcccc ccatgcgctc       180
accctccagt gcccggccag gcggacgcgg agccgcgcgg gtgacggcag aagcggctac       240
gcgcccagcc tagcccagcc cagcccagcc ggagaagagg gcgcgccgcg cccccgcccc       300
ccgccgctct ccagaggccg tgggtgcgga tgcgccgctg acgactcctg cgagagcacc       360
gcgcgcccta gcccgcagca tggcagccgc cgcctatgtg gaccactttg ccgccgagtg       420
cctcgtgtcc atgtccagcc gcgcagtcgt gcacgagccg cgggaaggac ctgaaccccg       480
gcccgagggc gcggccgccg ccgcccccac actgccccgc gttgacgagc gccgcgacgg       540
caaggacagc gcctcgcttt tcgtggtggc tcggatccta gcggacctca accagcaggc       600
gccggcgccc gcccccgcgg aacgcagaga aggggccgct gcgcgcaagg cgaggacccc       660
ctgccgcctg ccgcctgcgc cccctgcgcc gccacccggc ccagagcccg cctccccggg       720
acaagcaggc gcgccggccg cgcccccag ccccgcgtgg agcgagcccg aggcggcatt        780
ggagcaggaa cccggccccg cggggagcgg cgagcctggc tcagacaaa ggggtcggcg        840
aggccggagc cgcgcggacc tcgagtcccg cagaggaag cacaagtgcc actacgcggg        900
ctgcgagaaa gtttacggga aatcttcgca cctcaaggcg cacctgagaa ctcacacagg       960
```

-continued

```
tgagaggcct ttcgcctgca gctggcagga gtgcaacaag aagttcgcac gctcggacga    1020
gctggcacgg cactatcgca cgcacacggg cgagaagaag ttcagctgcc ccatctgtga    1080
gaagcgcttc atgcggagcg accacctgac gaagcacgca cgccgccacg ccaacttcca    1140
cccaggcatg ctgcagcggc gcggcggggg ctcgaggacc ggctcgctca gcgactacag    1200
ccgctccgat gccagcagcc ccaccatcag cccggccagc tcaccctgag cacccgcgcc    1260
tggaccgcgc ctcctcaccc ctttggtaat aggaaagctg agcgaacttg agaagtccac    1320
agcaaaacag ttttcttcac ctcaggtgtc aatttttaac aaaaagaaaa aaaaaaatct    1380
caaaaaaaaa agccctgacg tagctcgagc gaattcgata tcaagcttat cgataccgtc    1440
gacctcgggg ggggcccggt acccaattcg c                                  1471
```

RFLAT-1: A TRANSCRIPTION FACTOR THAT ACTIVATES RANTES GENE EXPRESSION

This application claims the benefit of U.S. Provisional Application 60/117,576, filed Jan. 27, 1999.

INTRODUCTION

1. Field of the Invention

The field of the invention is transcription factors, particularly zinc finger transcription factors, and more particularly transcription factors involved in the expression of RANTES.

2. Background of the Invention

Transcription factors are proteins that play a critical role in the regulation of eukaryotic gene expression. Transcription factors regulate expression of a gene by binding to sequence motifs positioned at various locations relative to the gene, where the resultant binding event modulates expression of the gene. Because of their role in the regulation of gene expression, the identification of transcription factors is of great interest in both research and industry as such factors are potential targets for therapeutic agents.

RANTES (Regulated upon Activation, Normal T cell Expressed and Secreted) is a member of the large and growing family of immunoregulatory cytokines called chemokines. The functions of chemokines include attracting blood leukocytes to sites of inflammation, regulating leukocyte maturation, trafficking and homing, and the development of lymphoid tissues. RANTES belongs to the C—C chemokine subfamily. It is a potent chemotactic agent for monocytes, T lymphocytes, basophils, and natural killer cells. It also causes degranulation of basophils, respiratory burst in eosinophils, and activation of T cells. Thus, RANTES appears to play an important role in both acute and chronic phases of inflammation.

RANTES and the closely related chemokines, macrophage inflammatory protein 1α (MIP-1α) and MIP-1β, may also play a role in resistance to human immunodeficiency virus (HIV) infection. It has been shown that RANTES, MIP-1α, and MIP-β inhibit infection of HIV in CD8+ T cells in vitro, and that these chemokines are highly expressed in some patients who are HIV+ but do not progress to AIDS. It has also been shown that the C—C chemokine receptor CC—CKR5, which selectively binds to these chemokines, is a co-receptor for HIV entry into target cells.

In normal T cells, expression of the RANTES gene is "late," occurring three to five days after activation. In the context of an immune response, late RANTES expression may be important in amplification and propagation of an inflammatory state. However, little is known about the molecular mechanisms underlying the induction of genes at this late stage of T cell activation.

Because RANTES plays a pivotal role in both acute and chronic inflammation and can block HIV infection in vitro, understanding the molecular basis for control of RANTES gene expression, especially in T cells, is of great interest.

Relevant Literature

Patent documents of interest include: WO 97/00266; 5,840,544 and 5,652,133.

Also of interest are: Nelson & Krensky, Current Opinion in Immunology (1998) 10: 265–270 and Baggiolini, Nature (1998) 392: 565–568.

SUMMARY OF THE INVENTION

A novel zinc finger transcription factore (RFLAT-1) and polypeptides related thereto, as well as nucleic acid compositions encoding the same, are provided. The subject polypeptide and nucleic acid compositions find use in a variety of applications, including diagnostic and therapeutic agent screening applications, as well as in treatment therapies. Also provided are methods of treating disease conditions associated with RANTES function, e.g. inflammation, and the like.

BRIEF DESCRIPTION OF THE FIGURES

FIG. 1 provides the nucleotide and deduced amino acid sequence of RFLAT-1 (SEQ ID NO:1). The three zinc fingers are underlined and the highly conserved cysteine and histidine residues are shown in boxes.

DETAILED DESCRIPTION OF THE INVENTION

Figure 2:
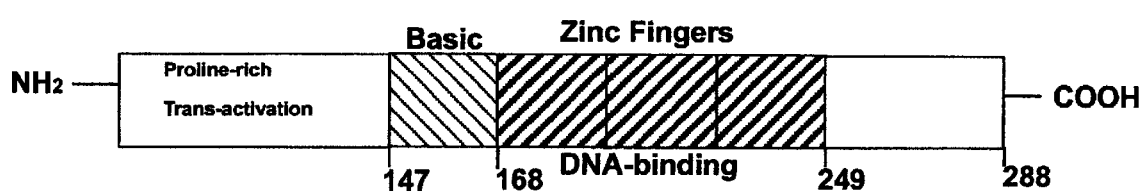
FIG. 2 provides a schematic diagram of the RFLAT-1 protein structure. The proline-rich transactivation domain, the three zinc fingers and the short basic region are represented by differently patterned boxes. The numbers indicate the first and last amino acid of each domain.

A novel zinc finger transcription factor (RFLAT-1) and polypeptides related thereto, as well as nucleic acid compositions encoding the same, are provided. The subject polypeptide and/or nucleic acid compositions find use in a variety of different applications, including diagnostic, and therapeutic agent screening/discovery/preparation applications. Also provided are methods of treating disease conditions associated with RANTES function, e.g. disease conditions characterized by the presence of inflammation, etc.

Before the subject invention is further described, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an," and "the" include plural reference unless the context clearly dictates otherwise. Unless defined otherwise, all technical and scientific terms used herein have the same meaning as commonly understood to one of ordinary skill in the art to which this invention belongs.

Nucleic Acid Compositions

RFLAT-1 nucleic acid compositions, as well as fragments thereof, are provided. By RFLAT-1 nucleic acid composition is meant a composition comprising a sequence of nucleotides having an open reading frame that encodes an RFLAT-1 protein, as described infra. Also encompassed in this term are nucleic acids that are homologous, substantially similar or identical to the RFLAT-1 nucleic acids, as described above. Thus, the subject invention provides genes encoding mammalian RFLAT-1 polypeptides, as well as homologs and fragments thereof.

Novel RFLAT-1 nucleic acid compositions of the invention of particular interest comprise an identifying sequence of nucleotide residues found in SEQ ID NO: 1, infra, where the identifying sequence of residues is at least about 10 nt in length, usually at least about 20 nt in length and more usually at least about 50 nt in length. Thus, the subject novel RFLAT-1 nucleic acid compositions include full length cDNAs that include an identifying sequence of nucleotides from SEQ ID NO: 1.

Of particular interest is the human RFLAT-1 gene. SEQ ID NO:01 provides the nucleotide sequence of a 1430 bp cDNA clone comprising the human DNA sequence encoding the full length human RFLAT-1. The cDNA clone whose sequence is provided as SEQ ID NO:01 comprises an open reading frame of 864 bp defined by an ATG start codon located at position 379–381 and a TGA stop codon located at position 1243–1245. The first methionine coding sequence is surrounded by a consensus Kozak sequence (GCCCGCAGCATGG) (SEQ ID NO:03). A cDNA clone encoding the murine RFLAT-1 protein is provided as SEQ ID NO:011, infra.

Also provided are homologs of RFLAT-1, where the source of homologous genes may be any species, particularly mammalian species e.g., primate species, particularly human; rodents, such as rats, canines, felines, bovines, ovines, equines, as well as non-mammalian species, e.g. yeast, nematodes, etc. Between mammalian species, e.g., human and mouse, homologs have substantial sequence similarity, e.g. at least 75% sequence identity, usually at least 90%, more usually at least 95% between nucleotide sequences. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et al. (1990), *J. Mol. Biol.* 215:403–10. Unless specified otherwise, all sequence analysis numbers provided herein are as determined with the BLAST program using default settings (i.e. parameters w=4 and T=17). The sequences provided herein are essential for recognizing RFLAT-1 related and homologous polynucleotides in database searches.

The subject RFLAT-1 nucleic acids may be cDNAs or genomic DNAs, as well as fragments thereof. The term "RFLAT-1 gene" shall be intended to mean the open reading frame encoding RFLAT-1 proteins and polypeptides, and introns of such genes, as well as adjacent 5' and 3' non-coding nucleotide sequences involved in the regulation of expression, up to about 20 kb beyond the coding region, but possibly further in either direction. The gene may be introduced into an appropriate vector for extrachromosomal maintenance or for integration into a host genome.

The term "cDNA" as used herein is intended to include all nucleic acids that share the arrangement of sequence elements found in native mature mRNA species, where sequence elements are exons and 3' and 5' non-coding regions. Normally mRNA species have contiguous exons, with the intervening introns, when present, being removed by nuclear RNA splicing, to create a continuous open reading frame encoding an SCN enriched protein.

A genomic sequence of interest comprises the nucleic acid present between the initiation codon and the stop codon, as defined in the listed sequences, including all of the introns that are normally present in a native chromosome. It may further include the 3' and 5' untranslated regions found in the mature mRNA. It may further include specific transcriptional and translational regulatory sequences, such as promoters, enhancers, etc., including about 1 kb, but possibly more, of flanking genomic DNA at either the 5' and 3' end of the transcribed region. The genomic DNA may be isolated as a fragment of 100 kbp or smaller; and substantially free of flanking chromosomal sequence. The genomic DNA flanking the coding region, either 3' and 5', or internal regulatory sequences as sometimes found in introns, contains sequences required for proper tissue and stage specific expression.

The nucleic acid compositions of the subject invention may encode all or a part of the subject RFLAT-1 proteins and polypeptides, described in greater detail infra. Double or single stranded fragments may be obtained from the DNA sequence by chemically synthesizing oligonucleotides in accordance with conventional methods, by restriction enzyme digestion, by PCR amplification, etc. For the most part, DNA fragments will be of at least 15 nt, usually at least 18 nt or 25 nt, and may be at least about 50 nt in length.

The RFLAT-1 genes of the subject invention are isolated and obtained in substantial purity, generally as other than an intact chromosome. Usually, the DNA will be obtained substantially free of other nucleic acid sequences that do not include an RFLAT-1 gene sequence or fragment thereof, generally being at least about 50%, usually at least about 90% pure and are typically "recombinant", i.e. flanked by one or more nucleotides with which it is not normally associated on a naturally occurring chromosome.

In addition to the plurality of uses described in greater detail in following sections, the subject nucleic acid compositions find use in the preparation of all or a portion of RFLAT-1 polypeptides, as described below.

Polypeptide Compositions

Also provided by the subject invention are RFLAT-1 polypeptide compositions. The term polypeptide composition as used herein refers to both the full length proteins as well as portions or fragments thereof. Also included in this term are variations of the naturally occurring proteins, where such variations are homologous or substantially similar to the naturally occurring protein, be the naturally occurring protein the human protein, mouse protein, or protein from some other species which naturally expresses an RFLAT-1 protein, usually a mammalian species. A candidate homologous protein is substantially similar to an RFLAT-1 protein of the subject invention, and therefore is an RFLAT-1 protein of the subject invention, if the candidate protein has a sequence that has at least about 80%, usually at least about 90% and more usually at least about 98% sequence identity with an RFLAT-1 protein, as measured by BLAST, supra. In the following description of the subject invention, the term "RFLAT-1-protein" is used to refer not only to the human RFLAT-1 protein, but also to homologs thereof expressed in non-human species, e.g. murine, rat and other mammalian species.

RFLAT-1 proteins of the subject invention are proteins capable of binding to the A site of the RANTES gene promoter. The proteins are characterized by having three tandem TFIIIA-like zinc fingers located at their C-terminus, and a transactivation domain at the N-terminus rich in proline and alanine residues. In addition, the subject RFLAT-1 proteins are phosphorylated. The overall structure of the subject RFLAT-1 proteins is similar to erythroid Krüppel-like factors (EKLF, BTEB, EZF). The subject RFLAT-1 proteins range in length from about 250 to 400 aa, usually from about 250 to 350 aa and more usually from about 250 to 300 aa, depending on the organism from which they are derived. As such, the molecular weight of the RFLAT-1 proteins may range from about 27.5 kD to 44 kD, usually from about 27.5 to 38.5 kD and more usually from about 27.5 to 33 kD.

Of particular interest is the human RFLAT-1 protein. In addition to the above characteristics, the human RFLAT-1 protein is a 288 amino acid polypeptide with a calculated molecular mass of 31,680 daltons. The human RFLAT-1 protein contains a 120 aa long C-terminal domain that contains three contiguous TFIIIA-like zinc finger motifs and shows a 73%, 72%, 65% and 65% sequence similarity to the analogous C-terminal domains of SP1, SP3, EKLF, and BTEB, respectively. Adjacent to the N-terminus of the zinc finger motif is a short sequence of 21 residues rich in basic amino acids. The remainder of the protein is proline rich (24/145 residues), serine rich (10/145 and alanine rich (30/145). The human RFLAT-1 protein has the amino acid sequence identified herein as SEQ ID NO:02.

The subject invention provides both phosphorylated and non-phosphorylated forms of the RFLAT-1 protein. Phosphorylated versions of the protein have a higher molecular weight than non-phosphorylated versions, where the molecular weight of the phosphorylated version ranges from about 32 to 40 kD, usually from about 32 to 38 kD.

In addition to the proteins described above, homologs or proteins (or fragments thereof) from other species, i.e. other animal or plant species, are also provided, where such homologs or proteins may be from a variety of different types of species, usually mammals, e.g. rodents, such as mice, rats; domestic animals, e.g. horse, cow, dog, cat; and humans. By homolog is meant a protein having at least about 35%, usually at least about 40% and more usually at least about 60% amino acid sequence identity with human RFLAT-1 as identified above (i.e. with a protein having the amino acid sequence of SEQ ID NO:02), where sequence identity is determined using the BLAST algorithm, supra.

The RFLAT-1 proteins of the subject invention are present in a non-naturally occurring environment, e.g are separated from their naturally occurring environment. In certain embodiments, the subject protein is present in a composition that is enriched for the protein as compared to a control, e.g. the cytoplasm of activated T-cells. As such, purified RFLAT-1 protein is provided, where by purified is meant that the protein is present in a composition that is substantially free of non RFLAT-1 proteins, where by substantially free is meant that less than 90%, usually less than 60% and more usually less than 50% of the composition is made up of non-RFLAT-1 enriched proteins.

In certain embodiments of interest, the subject protein is present in a composition that is substantially free of the constituents that are present in its naturally occurring environment. For example, a composition comprising a protein according to the subject invention in this embodiment will be substantially, if not completely, free of those other biological constituents, such as proteins, carbohydrates, lipids, etc., with which it is present in its natural environment. As such, protein compositions of these embodiments will necessarily differ from those that are prepared by purifying the protein from a naturally occurring source, where at least trace amounts of the protein's natural environment constituents will still be present in the composition prepared from the naturally occurring source.

The proteins of the subject invention may also be present as an isolate, by which is meant that the protein is substantially free of both non-RFLAT-1 proteins and other naturally occurring biologic molecules, such as oligosaccharides, polynucleotides and fragments thereof, and the like, where substantially free in this instance means that less than 70%, usually less than 60% and more usually less than 50% of the composition containing the isolated protein is a non-RFLAT-1 enriched naturally occurring biological molecule. In certain embodiments, the protein is present in substantially pure form, where by substantially pure form is meant at least 95%, usually at least 97% and more usually at least 99% pure.

In addition to the naturally occurring proteins, polypeptides which vary from the naturally occurring RFLAT-1 proteins are also provided. By RFLAT-1 polypeptides is meant proteins having an amino acid sequence encoded by an open reading frame (ORF) of an RFLAT-1 gene, described supra, including the full length protein and fragments thereof, particularly biologically active fragments and/or fragments corresponding to functional domains; and including fusions of the subject polypeptides to other proteins or parts thereof. Fragments of interest will typically be at least about 10 aa in length, usually at least about 50 aa in length, and may be as long as 300 aa in length or longer, but will usually not exceed about 1000 aa in length, where the fragment will have a stretch of amino acids that is identical to an RFLAT-1 protein encoded by a gene having the nucleic acid sequence of SEQ ID NO:01, or a homolog thereof; of at least about 10 aa, and usually at least about 15 aa, and in many embodiments at least about 50 aa in length.

Preparation of RFLAT-1 Polypeptides

The subject proteins and polypeptides may be obtained from naturally occurring sources, but are preferably synthetically produced. Where obtained from naturally occurring sources, the source chosen will generally be the activated T-lymphocytes of the species from which it is derived.

The subject polypeptide compositions may be synthetically derived by expressing a recombinant gene encoding the polypeptide, such as the polynucleotide compositions described above, in a suitable host. For expression, an expression cassette may be employed. The expression vector will provide a transcriptional and translational initiation region, which may be inducible or constitutive, where the coding region is operably linked under the transcriptional control of the transcriptional initiation region, and a transcriptional and translational termination region. These control regions may be native to the RFLAT-1 gene, or may be derived from exogenous sources.

Expression vectors generally have convenient restriction sites located near the promoter sequence to provide for the insertion of nucleic acid sequences encoding heterologous proteins. A selectable marker operative in the expression host may be present. Expression vectors may be used for the production of fusion proteins, where the exogenous fusion peptide provides additional functionality, i.e. increased protein synthesis, stability, reactivity with defined antisera, an enzyme marker, e.g. β-galactosidase, etc.

Expression cassettes may be prepared comprising a transcription initiation region, the gene or fragment thereof, and a transcriptional termination region. Of particular interest is the use of sequences that allow for the expression of functional epitopes or domains, usually at least about 8 amino acids in length, more usually at least about 15 amino acids in length, to about 25 amino acids, and up to the complete open reading frame of the gene. After introduction of the DNA, the cells containing the construct may be selected by means of a selectable marker, the cells expanded and then used for expression.

The proteins and polypeptides may be expressed in prokaryotes or eukaryotes in accordance with conventional ways, depending upon the purpose for expression. For large scale production of the protein, a unicellular organism, such as *E. coli, B. subtilis, S. cerevisiae*, insect cells in combination with baculovirus vectors, or cells of a higher organism such as vertebrates, particularly mammals, e.g. COS 7 cells, may be used as the expression host cells. In some situations, it is desirable to express the RFLAT-1 gene in eukaryotic cells, where the encoded protein will benefit from native folding and post-translational modifications. Small peptides can also be synthesized in the laboratory. Polypeptides that are subsets of the complete RFLAT-1 protein sequence may be used to identify and investigate parts of the protein important for function.

Once the source of the protein is identified and/or prepared, e.g. a transfected host expressing the protein is prepared, the protein is then purified to produce the desired protein comprising composition. Any convenient protein purification procedures may be employed, where suitable protein purification methodologies are described in Guide to Protein Purification, (Deuthser ed.) (Academic Press, 1990). For example, a lysate may be prepared from the original source, e.g. naturally occurring cells or tissues that express the protein or the expression host expressing the protein, and purified using HPLC, exclusion chromatography, gel electrophoresis, affinity chromatography, and the like.

Antibody Compositions

Also of interest are RFLAT-1 antibody compositions. Suitable antibodies are obtained by immunizing a host animal with peptides comprising all or a portion of a protein, such as found in the polypeptide compositions of the subject invention. Suitable host animals include mouse, rat sheep, goat, hamster, rabbit, etc. The origin of the protein immunogen may be mouse, human, rat, monkey etc. The host animal will generally be a different species than the immunogen, e.g human protein used to immunize mice, etc.

The immunogen may comprise the complete protein, or fragments and derivatives thereof. Preferred immunogens comprise all or a part of the protein, where these residues contain the post-translation modifications, such as glycosylation, found on the native protein. Immunogens comprising the extracellular domain are produced in a variety of ways known in the art, e.g. expression of cloned genes using conventional recombinant methods, isolation from HEC, etc.

For preparation of polyclonal antibodies, the first step is immunization of the host animal with a polypeptide, where the polypeptide will preferably be in substantially pure form, comprising less than about 1% contaminant. The immunogen may comprise the complete protein, fragments or derivatives thereof. To increase the immune response of the host animal, the protein may be combined with an adjuvant, where suitable adjuvants include alum, dextran, sulfate, large polymeric anions, oil & water emulsions, e.g. Freund's adjuvant, Freund's complete adjuvant, and the like. The protein may also be conjugated to synthetic carrier proteins or synthetic antigens. A variety of hosts may be immunized to produce the polyclonal antibodies. Such hosts include rabbits, guinea pigs, rodents, e.g. mice, rats, sheep, goats, and the like. The protein is administered to the host, usually intradermally, with an initial dosage followed by one or more, usually at least two, additional booster dosages. Following immunization, the blood from the host will be collected, followed by separation of the serum from the blood cells. The Ig present in the resultant antiserum may be further fractionated using known methods, such as ammonium salt fractionation, DEAE chromatography, and the like.

Monoclonal antibodies are produced by conventional techniques. Generally, the spleen and/or lymph nodes of an immunized host animal provide a source of plasma cells. The plasma cells are immortalized by fusion with myeloma cells to produce hybridoma cells. Culture supernatant from individual hybridomas is screened using standard techniques to identify those producing antibodies with the desired specificity. Suitable animals for production of monoclonal antibodies to the human protein include mouse, rat, hamster, etc. To raise antibodies against the mouse protein, the animal will generally be a hamster, guinea pig, rabbit, etc. The antibody may be purified from the hybridoma cell supernatants or ascites fluid by conventional techniques, e.g. affinity chromatography using RFLAT-1 protein bound to an insoluble support, protein A sepharose, etc.

The antibody may be produced as a single chain, instead of the normal multimeric structure. Single chain antibodies are described in Jost et al. (1994) *J.B.C.* 269:26267–73, and others. DNA sequences encoding the variable region of the heavy chain and the variable region of the light chain are ligated to a spacer encoding at least about 4 amino acids of small neutral amino acids, including glycine and/or serine. The protein encoded by this fusion allows assembly of a functional variable region that retains the specificity and affinity of the original antibody.

Humanized antibodies are also provided. Methods of humanizing antibodies are known in the art. The humanized antibody may be the product of an animal having transgenic human immunoglobulin constant region genes (see for example International Patent Applications WO 90/10077 and WO 90/04036). Alternatively, the antibody of interest may be engineered by recombinant DNA techniques to substitute the CH1, CH2, CH3, hinge domains, and/or the framework domain with the corresponding human sequence (see WO 92/02190).

The use of Ig cDNA for construction of chimeric immunoglobulin genes is known in the art (Liu et al. (1987) *P.N.A.S.* 84:3439 and (1987) *J. Immunol.* 139:3521). mRNA is isolated from a hybridoma or other cell producing the antibody and used to produce cDNA. The cDNA of interest may be amplified by the polymerase chain reaction using specific primers (U.S. Pat. Nos. 4,683,195 and 4,683,202). Alternatively, a library is made and screened to isolate the sequence of interest. The DNA sequence encoding the variable region of the antibody is then fused to human constant region sequences. The sequences of human constant regions genes may be found in Kabat et al. (1991) *Sequences of Proteins of Immunological Interest*, N. I. H. publication no. 91-3242. Human C region genes are readily available from known clones. The choice of isotype will be guided by the desired effector functions, such as complement fixation, or activity in antibody-dependent cellular cytotoxicity. Preferred isotypes are IgG1, IgG3 and IgG4. Either of the human light chain constant regions, kappa or lambda, may be used. The chimeric, humanized antibody is then expressed by conventional methods.

Antibody fragments, such as Fv, $F(ab')_2$ and Fab may be prepared by cleavage of the intact protein, e.g. by protease or chemical cleavage. Alternatively, a truncated gene is designed. For example, a chimeric gene encoding a portion of the $F(ab')_2$ fragment would include DNA sequences encoding the CH1 domain and hinge region of the H chain, followed by a translational stop codon to yield the truncated molecule.

Consensus sequences of H and L J regions may be used to design oligonucleotides for use as primers to introduce useful restriction sites into the J region for subsequent linkage of V region segments to human C region segments. C region cDNA can be modified by site directed mutagenesis to place a restriction site at the analogous position in the human sequence.

Expression vectors include plasmids, retroviruses, YACs, EBV derived episomes, and the like. A convenient vector is one that encodes a functionally complete human CH or CL immunoglobulin sequence, with appropriate restriction sites engineered so that any VH or VL sequence can be easily inserted and expressed. In such vectors, splicing usually occurs between the splice donor site in the inserted J region and the splice acceptor site preceding the human C region, and also at the splice regions that occur within the human CH exons. Polyadenylation and transcription termination occur at native chromosomal sites downstream of the coding regions. The resulting chimeric antibody may be joined to any strong promoter, including retroviral LTRs, e.g. SV-40 early promoter, (Okayama et al. (1983) *Mol. Cell. Bio.* 3:280), Rous sarcoma virus LTR (Gorman et al. (1982) *P.N.A.S.* 79:6777), and moloney murine leukemia virus LTR (Grosschedl et al. (1985) *Cell* 41:885); native Ig promoters, etc.

Uses or the Subject Polypeptide and Nucleic Acid Compositions

The subject polypeptide and nucleic acid compositions find use in a variety of different applications, including diagnostic and therapeutic agent screening, discovery and preparation applications, as well as in methods of modulating RANTES activity, where such methods find use in the treatment of conditions associated with RANTES activity, e.g. disease conditions characterized by inflammation, disease conditions in which the RANTES receptor is implicated, and the like.

General Applications

The subject nucleic acid compositions find use in a variety of different applications.

Applications of interest include: (a) the identification of RFLAT-1 gene homologs; (b) as a source of novel promoter elements; (c) the identification of RFLAT-1 expression regulatory factors; (d) as probes and primers in hybridization applications, e.g. PCR; (e) the identification of expression patterns in biological specimens; and (f) the preparation of cell or animal models for RFLAT-1 protein function; etc.

Identification of RFLAT-1 Nucleic Acid Homologs

Homologs of RFLAT-1 nucleic acids are identified by any of a number of methods. A fragment of the provided cDNA may be used as a hybridization probe against a cDNA library from the target organism of interest, where low stringency conditions are used. The probe may be a large fragment, or one or more short degenerate primers. Nucleic acids having sequence similarity are detected by hybridization under low stringency conditions, for example, at 50° C. and 6×SSC (0.9 M sodium chloride/0.09 M sodium citrate) and remain bound when subjected to washing at 55° C. in 1×SSC (0.15 M sodium chloride/0.015 M sodium citrate). Sequence identity may be determined by hybridization under stringent conditions, for example, at 50° C. or higher and 0.1×SSC (15 mM sodium chloride/01.5 mM sodium citrate). Nucleic acids having a region of substantial identity to the provided RFLAT-1 nucleic acid sequences, e.g. allelic variants, genetically altered versions of the gene, etc., bind to the provided RFLAT-1 sequences under stringent hybridization conditions. By using probes, particularly labeled probes of DNA sequences, one can isolate homologous or related genes.

Identification of Novel Promoter Elements

The sequence of the 5' flanking region may be utilized for promoter elements, including enhancer binding sites, that provide for regulation in tissues where the subject nucleic acids are expressed. The tissue specific expression is useful for determining the pattern of expression, and for providing promoters that mimic the native pattern of expression. Naturally occurring polymorphisms in the promoter region are useful for determining natural variations in expression, particularly those that may be associated with disease.

Identification of RFLAT-1 Gene Expression Regulatory Factors

Alternatively, mutations may be introduced into the promoter region to determine the effect of altering expression in experimentally defined systems. Methods for the identification of specific DNA motifs involved in the binding of transcriptional factors are known in the art, e.g sequence similarity to known binding motifs, gel retardation studies, etc. For examples, see Blackwell et al. (1995), *Mol. Med.* 1: 194–205; Mortlock et al. (1996), *Genome Res.* 6:327–33; and Joulin and Richard-Foy (1995), *Eur. J. Biochem.* 232:620–626.

The regulatory sequences may be used to identify cis acting sequences required for transcriptional or translational regulation of nucleic acid expression, especially in different tissues or stages of development, and to identify cis acting sequences and trans-acting factors that regulate or mediate nucleic acid expression. Such transcription or translational control regions may be operably linked to the RFLAT-1 gene in order to promote expression of wild type or altered RFLAT-1 or other proteins of interest in cultured cells, or in embryonic, fetal or adult tissues, and for gene therapy.

Probes and Primers

Small DNA fragments are useful as primers for PCR, hybridization screening probes, etc. Larger DNA fragments, i.e. greater than 100 nt, are useful for production of the encoded polypeptide, as described in the previous section. For use in amplification reactions, such as PCR, a pair of primers will be used. The exact composition of the primer sequences is not critical to the invention, but for most applications the primers will hybridize to the subject sequence under stringent conditions, as known in the art. It is preferable to choose a pair of primers that will generate an amplification product of at least about 50 nt, preferably at least about 100 nt. Algorithms for the selection of primer sequences are generally known, and are available in commercial software packages. Amplification primers hybridize to complementary strands of DNA, and will prime towards each other.

Identification of Expression Patterns in Biological Specimens

The DNA may also be used to identify expression of the gene in a biological specimen. The manner in which one probes cells for the presence of particular nucleotide sequences, as genomic DNA or RNA, is well established in the literature. Briefly, DNA or mRNA is isolated from a cell sample. The mRNA may be amplified by RT-PCR, using reverse transcriptase to form a complementary DNA strand, followed by polymerase chain reaction amplification using primers specific for the subject DNA sequences. Alternatively, the mRNA sample is separated by gel electrophoresis, transferred to a suitable support, e.g. nitrocellulose, nylon, etc., and then probed with a fragment of the subject DNA as a probe. Other techniques, such as oligonucleotide ligation assays, in situ hybridizations, and hybridization to DNA probes arrayed on a solid chip may also find use. Detection of mRNA hybridizing to the subject sequence is indicative of RFLAT-1 gene expression in the sample.

The Preparation of Mutants

The sequence of an RFLAT-1 gene, including flanking promoter regions and coding regions, may be mutated in various ways known in the art to generate targeted changes in promoter strength, sequence of the encoded protein, etc. The DNA sequence or protein product of such a mutation will usually be substantially similar to the sequences provided herein, i.e. will differ by at least one nucleotide or amino acid, respectively, and may differ by at least two but not more than about ten nucleotides or amino acids. The sequence changes may be substitutions, insertions, deletions, or a combination thereof. Deletions may further include larger changes, such as deletions of a domain or exon. Other modifications of interest include epitope tagging, e.g. with the FLAG system, HA, etc. For studies of subcellular localization, fusion proteins with green fluorescent proteins (GFP) may be used.

Techniques for in vitro mutagenesis of cloned genes are known. Examples of protocols for site specific mutagenesis may be found in Gustin et al. (1993), *Biotechniques* 14:22; Barany (1985), *Gene* 37:111–23; Colicelli et al. (1985), *Mol. Gen. Genet.* 199:537–9; and Prentki et al. (1984), *Gene* 29:303–13. Methods for site specific mutagenesis can be found in Sambrook et al., *Molecular Cloning: A Laboratory Manual*, CSH Press 1989, pp. 15.3–15.108; Weiner et al. (1993), *Gene* 126:35–41; Sayers et al. (1992), *Biotechniques* 13:592–6; Jones and Winistorfer (1992), *Biotechniques* 12:528–30; Barton et al. (1990), *Nucleic Acids Res* 18:7349–55; Marotti and Tomich (1989), *Gene Anal. Tech.* 6:67–70; and Zhu (1989), *Anal Biochem* 177:120–4. Such mutated genes may be used to study structure-function relationships of the RFLAT-1 protein, or to alter properties of the protein that affect its function or regulation.

Production of In Vivo Models of RFLAT-1 Protein Function

The subject nucleic acids can be used to generate transgenic, non-human animals or site specific gene modifications in cell lines. Transgenic animals may be made through homologous recombination, where the normal locus of the particular gene of interest is altered. Alternatively, a nucleic acid construct is randomly integrated into the genome. Vectors for stable integration include plasmids, retroviruses and other animal viruses, YACs, and the like.

The modified cells or animals are useful in the study of RFLAT-1 gene function and regulation. For example, a series of small deletions and/or substitutions may be made in the host's native gene to determine the role of different exons in RFLAT-1 activity. Specific constructs of interest include anti-sense nucleic acid compositions, which will block gene expression, expression of dominant negative mutations, and over-expression of genes. Where a particular sequence is introduced, the introduced sequence may be either a complete or partial sequence of a gene native to the host, or may be a complete or partial sequence that is exogenous to the host animal, e.g., a human RFLAT-1 sequence. A detectable marker, such as lac Z, may be introduced into the locus, where upregulation of gene expression will result in an easily detected change in phenotype.

One may also provide for expression of the RFLAT-1 gene or variants thereof in cells or tissues where it is not normally expressed, at levels not normally present in such cells or tissues, or at abnormal times of development.

DNA constructs for homologous recombination will comprise at least a portion of the gene native to the species of the host animal, wherein the gene has the desired genetic modification(s), and includes regions of homology to the target locus. DNA constructs for random integration need not include regions of homology to mediate recombination. Conveniently, markers for positive and negative selection are included. Methods for generating cells having targeted gene modifications through homologous recombination are known in the art. For various techniques for transfecting mammalian cells, see Keown et al. (1990), *Meth. Enzymol.* 185:527–537.

For embryonic stem (ES) cells, an ES cell line may be employed, or embryonic cells may be obtained freshly from a host, e.g mouse, rat, guinea pig, etc. Such cells are grown on an appropriate fibroblast-feeder layer or grown in the presence of leukemia inhibiting factor (LIF). When ES or embryonic cells have been transformed, they may be used to produce transgenic animals. After transformation, the cells are plated onto a feeder layer in an appropriate medium. Cells containing the construct may be detected by employing a selective medium. After sufficient time for colonies to grow, they are picked and analyzed for the occurrence of homologous recombination or integration of the construct. Those colonies that are positive may then be used for embryo manipulation and blastocyst injection. Blastocysts are obtained from 4 to 6 week old superovulated females. The ES cells are trypsinized, and the modified cells are injected into the blastocoel of the blastocyst. After injection, the blastocysts are returned to each uterine horn of pseudopregnant females. Females are then allowed to go to term and the resulting offspring screened for the construct. By providing for a different phenotype of the blastocyst and the genetically modified cells, chimeric progeny can be readily detected.

The chimeric animals are screened for the presence of the modified gene and males and females having the modification are mated to produce homozygous progeny. If the gene alterations cause lethality at some point in development, tissues or organs can be maintained as allogeneic or congenic grafts or transplants, or in in vitro culture. The transgenic animals may be any non-human mammal, such as laboratory animals, domestic animals, etc. The transgenic animals may be used in functional studies, drug screening, etc., e.g. to determine the effect of a candidate drug on RFLAT-1 activity.

Diagnostic Applications

Also provided are methods of diagnosing disease states associated with the RFLAT-1 activity, e.g. based on observed levels of an RFLAT-1 protein or the expression level of the RFLAT-1 gene in a biological sample of interest. Samples, as used herein are fluids derived from cells, tissues or organs. Also included in the term are derivatives and fractions of such fluids.

A number of methods are available for determining the expression level of a gene or protein in a particular sample. Diagnosis may be performed by a number of methods to determine the absence or presence or altered amounts of normal or abnormal protein in a patient sample. For example, detection may utilize staining of cells or histological sections with labeled antibodies (RFLAT-1 antibodies being described above), performed in accordance with conventional methods. Cells are permeabilized to stain cytoplasmic molecules. The antibodies of interest are added to the cell sample, and incubated for a period of time sufficient to allow binding to the epitope, usually at least about 10 minutes. The antibody may be labeled with radioisotopes, enzymes, fluorescers, chemiluminescers, or other labels for direct detection. Alternatively, a second stage antibody or reagent is used to amplify the signal. Such reagents are well known in the art. For example, the primary antibody may be conjugated to biotin, with horseradish peroxidase-conjugated avidin added as a second stage reagent. Alternatively, the secondary antibody conjugated to a flourescent compound, e.g fluorescein, rhodamine, Texas red, etc. Final detection uses a substrate that undergoes a color change in the presence of the peroxidase. The absence or presence of antibody binding may be determined by various methods, including flow cytometry of dissociated cells, microscopy, radiography, scintillation counting, etc.

Alternatively, one may focus on the expression of an RFLAT-1 gene. Biochemical studies may be performed to determine whether a sequence polymorphism in a coding region or control regions is associated with disease. Disease associated polymorphisms may include deletion or truncation of the gene, mutations that alter expression level, that affect the activity of the protein, etc.

Changes in the promoter or enhancer sequence that may affect expression levels of an RFLAT-1 gene can be compared to expression levels of the normal allele by various methods known in the art. Methods for determining promoter or enhancer strength include quantitation of the expressed natural protein; insertion of the variant control element into a vector with a reporter gene such as β-galactosidase, luciferase, chloramphenicol acetyltransferase, etc. that provides for convenient quantitation; and the like.

A number of methods are available for analyzing nucleic acids for the presence of a specific sequence, e.g. a disease associated polymorphism. Where large amounts of DNA are available, genomic DNA is used directly. Alternatively, the region of interest is cloned into a suitable vector and grown in sufficient quantity for analysis. Cells that express an SCN enriched gene may be used as a source of mRNA, which may be assayed directly or reverse transcribed into cDNA for analysis. The nucleic acid may be amplified by conventional techniques, such as the polymerase chain reaction (PCR), to provide sufficient amounts for analysis. The use of the polymerase chain reaction is described in Saiki, et al. (1985), *Science* 239:487, and a review of techniques may be found in Sambrook, et al. *Molecular Cloning: A Laboratory Manual*, CSH Press 1989, pp. 14.2–14.33. Alternatively, various methods are known in the art that utilize oligonucleotide ligation as a means of detecting polymorphisms, for examples see Riley et al. (1990), *Nucl. Acids Res.* 18:2887–2890; and Delahunty et al. (1996), *Am. J. Hum. Genet.* 58:1239–1246.

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}$P, $^{35}$S, $^{3}$H; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

The sample nucleic acid, e.g. amplified or cloned fragment, is analyzed by one of a number of methods known in the art. The nucleic acid may be sequenced by dideoxy or other methods, and the sequence of bases compared to a wild-type RFLAT-1 sequence. Hybridization with the variant sequence may also be used to determine its presence, by Southern blots, dot blots, etc. The hybridization pattern of a control and variant sequence to an array of oligonucleotide probes immobilized on a solid support, as described in U.S. Pat. No. 5,445,934, or in WO 95/35505, may also be used as a means of detecting the presence of variant sequences. Single strand conformational polymorphism (SSCP) analysis, denaturing gradient gel electrophoresis (DGGE), and heteroduplex analysis in gel matrices are used to detect conformational changes created by DNA sequence variation as alterations in electrophoretic mobility. Alternatively, where a polymorphism creates or destroys a recognition site for a restriction endonuclease, the sample is digested with that endonuclease, and the products size fractionated to determine whether the fragment was digested. Fractionation is performed by gel or capillary electrophoresis, particularly acrylamide or agarose gels.

Screening for mutations in an RFLAT-1 gene may be based on the functional or antigenic characteristics of the protein. Protein truncation assays are useful in detecting deletions that may affect the biological activity of the protein. Various immunoassays designed to detect polymorphisms in proteins may be used in screening. Where many diverse genetic mutations lead to a particular disease phenotype, functional protein assays have proven to be effective screening tools. The activity of the encoded protein may be determined by comparison with the wild-type protein.

Diagnostic methods of the subject invention in which the level of expression of an RFLAT-1 gene is of interest will typically involve comparison of the nucleic acid abundance of a sample of interest with that of a control value to determine any relative differences in the expression of the gene, where the difference may be measured qualitatively and/or quantitatively, which differences are then related to the presence or absence of an abnormal expression pattern. A variety of different methods for determining the nucleic acid abundance in a sample are known to those of skill in the art, where particular methods of interest include those described in: Pietu et al., Genome Res. (June 1996) 6: 492–503; Zhao et al., Gene (Apr. 24, 1995) 156: 207–213; Soares , Curr. Opin. Biotechnol. (October 1997) 8: 542–546; Raval, J. Pharmacol Toxicol Methods (November 1994) 32: 125–127; Chalifour et al., Anal. Biochem (Feb. 1, 1994) 216: 299–304; Stolz & Tuan, Mol. Biotechnol. (December 19960 6: 225–230; Hong et al., Bioscience Reports (1982) 2: 907; and McGraw, Anal. Biochem. (1984) 143: 298. Also of interest are the methods disclosed in WO 97/27317, the disclosure of which is herein incorporated by reference.

Screening Assays

The subject polypeptides find use in various screening assays designed to identify therapeutic agents, e.g. agents having anti-inflammatory activity, agents having anti-HIV activity, agents having anti-neoplastic acitivty, etc. The screening methods will typically be assays which provide for qualitative/quantitative measurements of protein activity in the presence of a particular candidate therapeutic agent. For example, the assay could be an assay which measures the activity of a protein in the presence and absence of a candidate inhibitor agent, e.g. the expression of RANTES in the presence or absence of a candidate agent. The screening method may be an in vitro or in vivo format, where both formats are readily developed by those of skill in the art. Depending on the particular method, one or more of, usually one of, the components of the screening assay may be labeled, where by labeled is meant that the components comprise a detectable moiety, e.g. a fluorescent or radioactive tag, or a member of a signal producing system, e.g. biotin for binding to an enzyme-streptavidin conjugate in which the enzyme is capable of converting a substrate to a chromogenic product.

A variety of other reagents may be included in the screening assay. These include reagents like salts, neutral proteins, e.g. albumin, detergents, etc that are used to facilitate optimal protein-protein binding and/or reduce non-specific or background interactions. Reagents that improve the efficiency of the assay, such as protease inhibitors, nuclease inhibitors, anti-microbial agents, etc. may be used.

A variety of different candidate agents may be screened by the above methods. Candidate agents encompass numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

Candidate agents are obtained from a wide variety of sources including libraries of synthetic or natural compounds. For example, numerous means are available for random and directed synthesis of a wide variety of organic compounds and biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Nucleic Acid and Polypeptide Therapeutic Compositions

The nucleic acid compositions of the subject invention also find use as therapeutic agents in situations where one wishes to enhance the activity of an RFLAT-1 protein activity in a host, e.g. in a mammalian host in which the activity of an RFLAT-1 protein is sufficiently low such that a disease condition is present, etc. The genes, gene fragments, or the encoded protein or protein fragments are useful in gene therapy to treat disorders associated with gene defects or disease condition in which enhanced gene activity is desired Expression vectors may be used to introduce the RFLAT-1 gene into a cell. Such vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks.

The gene or protein may be introduced into tissues or host cells by any number of routes, including viral infection, microinjection, or fusion of vesicles. Jet injection may also be used for intramuscular administration, as described by Furth et al. (1992), *Anal Biochem* 205:365–368. The DNA may be coated onto gold microparticles, and delivered intradermally by a particle bombardment device, or "gene gun" as described in the literature (see, for example, Tang et al. (1992), *Nature* 356:152–154), where gold microprojectiles are coated with the DNA and then bombarded into skin cells.

Methods of Modulating RFLAT-1 Activity in a Host

Also provided are methods of modulating the RFLAT-1 activity in a host, e.g. modulating the functions of the RFLAT-1 in a host, e.g. the RANTES expression regulatory activity of RFLAT-1. Generally, such methods will be premised on modulating the activity of the RFLAT-1 protein, either enhancing or inhibiting the activity of the protein. For the modulation of RFLAT-1 protein activity in vivo in a host, an effective amount of an active agent that modulates the activity, e.g. reduces the activity, of the protein in vivo, is administered to the host. The active agent may be a variety of different compounds, including a naturally occurring or synthetic small molecule compound, an antisense composition, and the like.

Naturally occurring or synthetic small molecule compounds of interest include numerous chemical classes, though typically they are organic molecules, preferably small organic compounds having a molecular weight of more than 50 and less than about 2,500 daltons. Candidate agents comprise functional groups necessary for structural interaction with proteins, particularly hydrogen bonding, and typically include at least an amine, carbonyl, hydroxyl or carboxyl group, preferably at least two of the functional chemical groups. The candidate agents often comprise cyclical carbon or heterocyclic structures and/or aromatic or polyaromatic structures substituted with one or more of the above functional groups. Candidate agents are also found among biomolecules including peptides, saccharides, fatty acids, steroids, purines, pyrimidines, derivatives, structural analogs or combinations thereof.

In yet other embodiments of the invention, the active agent is an agent that modulates, and generally decreases or down regulates, the expression of the RFLAT-1 gene in the host. Antisense molecules can be used to down-regulate expression of genes in cells. The anti-sense reagent may be antisense oligonucleotides (ODN), particularly synthetic ODN having chemical modifications from native nucleic acids, or nucleic acid constructs that express such anti-sense molecules as RNA. The antisense sequence is complementary to the mRNA of the targeted gene, and inhibits expression of the targeted gene products. Antisense molecules inhibit gene expression through various mechanisms, e.g. by reducing the amount of mRNA available for translation, through activation of RNAse H, or steric hindrance. One or a combination of antisense molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like. It has been found that short oligonucleotides, of from 7 to 8 bases in length, can be strong and selective inhibitors of gene expression (see Wagner et al. (1996), *Nature Biotechnol.* 14:840–844).

A specific region or regions of the endogenous sense strand mRNA sequence is chosen to be complemented by the antisense sequence. Selection of a specific sequence for 20 the oligonucleotide may use an empirical method, where several candidate sequences are assayed for inhibition of expression of the target gene in an in vitro or animal model. A combination of sequences may also be used, where several regions of the mRNA sequence are selected for antisense complementation.

Antisense oligonucleotides may be chemically synthesized by methods known in the art (see Wagner et al. (1993), supra, and Milligan et al., supra.) Preferred oligonucleotides are chemically modified from the native phosphodiester structure, in order to increase their intracellular stability and binding affinity. A number of such modifications have been described in the literature, which alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

As an alternative to anti-sense inhibitors, catalytic nucleic acid compounds, e.g. ribozymes, anti-sense conjugates, etc. may be used to inhibit gene expression. Ribozymes may be synthesized in vitro and administered to the patient, or may be encoded on an expression vector, from which the ribozyme is synthesized in the targeted cell (for example, see International patent application WO 9523225, and Beigelman et al. (1995), *Nucl. Acids Res.* 23:4434–42). Examples of oligonucleotides with catalytic activity are described in WO 9506764. Conjugates of anti-sense ODN with a metal complex, e.g. terpyridylCu(II), capable of mediating mRNA hydrolysis are described in Bashkin et al. (1995), *Appl. Biochem. Biotechnol.* 54:43–56.

As mentioned above, an effective amount of the active agent is administered to the host, where "effective amount" means a dosage sufficient to produce a desired result, where the desired result in the desired modulation, e.g. enhancement, reduction, of the target protein activity.

In the subject methods, the active agent(s) may be administered to the host using any convenient means capable of resulting in the desired target protein activity modulation. Thus, the agent can be incorporated into a variety of formulations for therapeutic administration. More particularly, the agents of the present invention can be formulated into pharmaceutical compositions by combination with appropriate, pharmaceutically acceptable carriers or diluents, and may be formulated into preparations in solid, semi-solid, liquid or gaseous forms, such as tablets, capsules, powders, granules, ointments, solutions, suppositories, injections, inhalants and aerosols.

As such, administration of the agents can be achieved in various ways, including oral, buccal, rectal, parenteral, intraperitoneal, intradermal, transdermal, intracheal,etc., administration.

In pharmaceutical dosage forms, the agents may be administered in the form of their pharmaceutically acceptable salts, or they may also be used alone or in appropriate association, as well as in combination, with other pharmaceutically active compounds. The following methods and excipients are merely exemplary and are in no way limiting.

For oral preparations, the agents can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The agents can be formulated into preparations for injection by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives.

The agents can be utilized in aerosol formulation to be administered via inhalation. The compounds of the present invention can be formulated into pressurized acceptable propellants such as dichlorodifluoromethane, propane, nitrogen and the like.

Furthermore, the agents can be made into suppositories by mixing with a variety of bases such as emulsifying bases or water-soluble bases. The compounds of the present invention can be administered rectally via a suppository. The suppository can include vehicles such as cocoa butter, carbowaxes and polyethylene glycols, which melt at body temperature, yet are solidified at room temperature.

Unit dosage forms for oral or rectal administration such as syrups, elixirs, and suspensions may be provided wherein each dosage unit, for example, teaspoonful, tablespoonful, tablet or suppository, contains a predetermined amount of the composition containing one or more inhibitors. Similarly, unit dosage forms for injection or intravenous administration may comprise the inhibitor(s) in a composition as a solution in sterile water, normal saline or another pharmaceutically acceptable carrier.

The term "unit dosage form," as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle.

The specifications for the novel unit dosage forms of the present invention depend on the particular compound employed and the effect to be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

Where the agent is a polypeptide, polynucleotide, analog or mimetic thereof, e.g. antisense composition, it may be introduced into tissues or host cells by any number of routes, including viral infection, microinjection, or fusion of vesicles. Jet injection may also be used 15 for intramuscular administration, as described by Furth et al. (1992), *Anal Biochem* 205:365–368. The DNA may be coated onto gold microparticles, and delivered intradermally by a particle bombardment device, or "gene gun" as described in the literature (see, for example, Tang et al. (1992), *Nature* 356:152–154), where gold microprojectiles are coated with the DNA, then bombarded into skin cells.

Those of skill in the art will readily appreciate that dose levels can vary as a function of the specific compound, the severity of the symptoms and the susceptibility of the subject to side effects. Preferred dosages for a given compound are readily determinable by those of skill in the art by a variety of means.

The subject methods find use in the treatment of a variety of different conditions involving RFLAT-1 protein activity, including both insufficient or hypo-protein activity and hyper-protein activity. Thus, the subject methods find use in situations where the modulation of RFLAT-1 function is desired. Generally, the subject methods find use in the treatment of disease conditions involving RANTES gene expression, where such conditions include conditions in which suppression of RANTES gene expression is desired, e.g. those disease conditions characterized by the presence of acute and chronic inflammation, autoimmune diseases; as well as disease conditions in which enhancement of RANTES gene expression is desired, e.g. AIDS, neoplastic dieases etc.

By treatment is meant that at least an amelioration of the symptoms associated with the condition afflicting the host, where amelioration is used in a broad sense to refer to at least a reduction in the magnitude of a parameter, e.g. symptom (such as inflammation), associated with the condition being treated, such as insomnia or jet lag, etc. As such, treatment also includes situations where the pathological condition, or at least symptoms associated therewith, are completely inhibited, e.g. prevented from happening, or stopped, e.g. terminated, such that the host no longer suffers from the condition, or at least the symptoms that characterize the condition.

A variety of hosts are treatable according to the subject methods. Generally such hosts are "mammals" or "mammalian," where these terms are used broadly to describe organisms which are within the class mammalia, including the orders carnivore (e.g., dogs and cats), rodentia (e.g., mice, guinea pigs, and rats), and primates (e.g., humans, chimpanzees, and monkeys). In many embodiments, the hosts will be humans.

Kits with unit doses of the active agent, usually in oral or injectable doses, are provided. In such kits, in addition to the containers containing the unit doses will be an informational package insert describing the use and attendant benefits of the drugs in treating pathological condition of interest. Preferred compounds and unit doses are those described herein above.

The following examples are offered primarily for purposes of illustration. It will be readily apparent to those skilled in the art that the formulations, dosages, methods of administration, and other parameters of this invention may be further modified or substituted in various ways without departing from the spirit and scope of the invention.

EXPERIMENTAL

I. Experimental Procedures

A. Nuclear Extract Preparation and Southwestern Blotting

Human PBL were isolated over Ficoll-Hypaque (ICN Biomedicals, Inc., Costa Mesa, Calif.). Cells ($2 \times 10^6$/ml) were stimulated with 5 µg/ml PHA (DIFCO, Detroit, Mich.) in RPMI Medium 1640 (Irvine Scientific, Santa Ana, Calif.) supplemented with 10% FCS (HyClone, Logan, Utah)/2 mM L-glutamine, 100 U/ml penicillin, 100 µg/ml streptomycin (Irvine Scientific, Santa Ana, Calif.) for up to 7 days. Nuclear and cytosolic extracts were prepared as described (Durand, et al., (1988) Mol. Cell. Biol. 8, 1715–1724.), with minor modifications (Ortiz et al., (1996) Mol. Cell. Biol. 16, 202–210). The protein concentration of the extracts was determined by Bradford assay using the Bio-Rad protein assay reagent. Nuclear extracts were prepared from resting PBL, PHA activated PBL at days 1–7, AJY-CTL, "mature" T tumor line Hut 78 and B lymphoblastoid JY cells. 50 µg of each nuclear extract was separated by 10% SDS-PAGE and the proteins were transferred onto a PVDF membrane. The membrane was then subjected to a denaturation-renaturation procedure by incubation in binding buffer (10 mM Tris-Cl, pH 7.5, 80 mM NaCl, 1 mM EDTA, 1 mM dithiothreitol, 1% glycerol) supplemented with decreasing amounts of guanidine (6 M, 4.5 M, 2.25 M, 1.13 M, 0.56 M, 0.28 M, 0.14 M, and 0 M) at 0° C. The membrane was blocked with 5% non-fat milk in binding buffer, hybridized with $^{32}$p end-labeled A/B oligonucleotide (0.1–0.2 pmole/ml in 0.25% non-fat milk in binding buffer) at 25° C. for 5 hours, washed, and exposed to Amersham Hyperfilm at −80° C. for 3 days.

B. Library Construction and Screening

PBL were cultured with PHA-P for 5 days and total RNA was extracted (Chomczynski and Sacchi, (1987) Anal. Biochem. 162, 156–159.). Poly(A)+ RNA was further isolated using a QIAGEN kit (QIAGEN Inc., Santa Clarita, Calif.). 5 µg of poly(A)+ RNA was used to construct a λgt11 library using the SuperScript™ Choice System (Life Technologies, Gaithersburg, Md.). The recombinant lambda phage were packaged with Gigapack®III Gold Packaging Extract (Stratagene, La Jolla, Calif.) and amplified. For expression cloning, lambda phage plaques were induced with IPTG at 37° C. for 6 hours and transferred to PVDF membranes. The denaturation-renaturation treatment and hybridization protocol was the same as that for Southwestern blotting except that hybridization was only for one hour at 25° C., and the binding buffer was supplemented with 10 µg/ml of denatured, sonicated calf thymus DNA. A total of 6×10$^6$ (3×library complexity) plaques were screened with a $^{32}$P end-radiolabeled A3 oligonucleotide. The oligonucleotide sequence was: GGGAATTCGAATTCGCTATTTTG-GAAACTCCCCTTAGGGCTATTTTGGAAACTC CCCT-TAGGGCTATTTTGGAAACTCCCCTTAG-GCTCGAGCTCGAGGG (SEQ ID NO:04). Positive phage clones were isolated and phage DNA was purified with a Wizard® Lambda Preps DNA Purification System (Promega, Madison, Wis.). The cDNAs were excised from the λgt11 vector by restriction digestion and subcloned into a plasmid vector for sequencing. The same library was used for DNA-DNA screening following the protocols described by Ausubel et al., (1989). Current protocols in molecular biology (New York City, N.Y.: Wiley Interscience ). 2.4×10$^6$ plaques were screened with a $^{32}$P randomly labeled 880 bp cDNA fragment from RFLAT-1 to obtain the 1430 bp complete sequence.

C. Northern Blotting

Total RNA and poly(A)+ RNA was isolated as described above. Multi-human tissue blots with poly(A)+ RNA were purchased from Clontech (Palo Alto, Calif.). Using Clontech ExpressHyb Hybridization solution, Northern blots were probed with the RFLAT-1 cDNA fragment or human β-actin cDNA under high-stringency conditions according to the manufacturer's instructions. Specifically, the Northern blot was first probed with the RFLAT-1 cDNA fragment, stripped and then probe with the β-actin cDNA to normalize for the amount of RNA.

D. Transient Transfections and Luciferase Reporter Gene Assays

A series of RANTES promoter pGL2-luciferase reporter constructs were described previously (Nelson et al., (1993) J. Immunol. 151, 2601–2612.; Ortiz et al., 1996, supra). RFLAT-1 cDNA (EcoR I fragment) was excised from the λgt11 vector and subcloned into the CMV-promoter driven mammalian expression vector pcDNA3.1(+) (Invitrogen, San Diego, Calif.). p65 cDNA (Hind III-BamH I fragment) and p50 cDNA (Hind III-Xba I fragment) were excised from pBluescript vector (gifts from G. Nolan, Stanford University) and subcloned into pcDNA 3.1. COS-7 and NIH3T3 fibroblasts were transiently transfected by the calcium phosphate method (Sambrook et al. (1989). Molecular cloning, a laboratory manual, second edition (Cold Spring Harbor, N.Y.: Cold Spring Harbor Laboratory Press)). Jurkat T cells were transiently transfected by electroporation as described previously (Nelson et al., 1993, supra). 36 hours after transfection, the cells were harvested and luciferase activity was determined using a Luciferase Assay System Kit (Promega, Madison, Wis.) following the manufacturer's instructions. Luciferase activity was measured over 30 seconds in a Wallac/EG&G Lumat LB 9507 Luminometer. Transfection efficiency was normalized by protein content using Bradford protein assays. In some transfections, CMV-lacZ plasmid was cotransfected to determine transfection efficiency and β-Galactosidase assays were performed according to the instructions accompanying the reporter lysis buffer reagent.

E. Western Blotting and In Vitro Transcription/Translation Assay

The 880 bp fragment of the RFLAT-1 cDNA was fused into the pET-28a(+) vector to enerate the expression vector.

The pET-RFLAT-1 plasmid was transformed into bacterial strain BL21(DE3)plysS and protein expression was induced by Isopropyl-β-D-thiogalactoside (IPTG). Bacterial pellets were dissolved in 6 M guanidine-HCl/0.05 M Tris-HCl and lysed by sonication. Recombinant His$_6$-RFLAT-1 was purified using a Ni$^+$ column and refolded in 5×volume of buffer containing 0.75 M Arginine, 0.05 M Tris-HCl, pH 8.0, 0.05 M KCl, and 0.0001 M EDTA. Proteins were then dialyzed against PBS and concentrated. His$_6$-RFLAT-1 was injected into rabbits to generate polyclonal antibodies. Anti-RFLAT-1 antiserum was purified over a protein A column followed by an antigen column. For Western blots of transfected cells, cultures were harvested 36 hours after transfection and nuclear extracts were prepared according to Andrews and Faller, (1991) Nucleic Acids Res. 19(9):2499. For PBL and other cell lines, nuclear extracts were prepared as described above. Anti-RFLAT-1 Western blotting was performed as follows: membranes were blocked in 5% non-fat milk in TBST (0.02 M Tris-HCl, pH 7.4, 0.5 M NaCl, 0.2% Tween-20), washed with TBST, and incubated in blocking buffer containing antigen purified anti-RFLAT-1 (1:1000 [v/v]). The membranes were then washed, incubated in blocking buffer with horseradish peroxidase conjugated goat anti-rabbit antibodies (1:10,000 [v/v]), washed, detected by ECL (Amersham, Arlington Heights, Ill.), and exposed to Amersham Hyperfilm. Anti-p50 and anti-p65 Western blotting was performed following the manufacturer's instructions. In vitro transcription/translation assays were performed using the TNT® Quick Coupled Transcription/Translation System (Promega, Madison, Wis.) following the instructions.

F. Immunostaining and EMSA

1×10$^4$ cells were adhered to 8 well slides (Electron Microscopy Sciences, Ft. Washington, Pa.) and fixed in methanol followed by acetone. The wells were incubated in blocking buffer (5% goat serum, 5% horse serum, 0.1% Triton X-100 in PBS), washed in PBS supplemented with 0.1% Triton X-100, and incubated with antigen purified rabbit polyclonal anti-RFLAT-1 (1:500 [v/v]) or rabbit IgG (1:500 [v/v]) (Santa Cruz Biotechnology, Santa Cruz, Calif.). The wells were washed, incubated with goat anti-rabbit FITC (1:2000 [v/v]) (Caltag, Burlingame, Calif.), and anti-FITC Alexa™ 488 (1:2000 [v/v]) (Molecular Probes, Eugene, Oreg.). Finally, the slide was washed with PBS, covered with mounting media (1:3 [v/v], Vectashield with propidium iodide) (Vector, Burlingame, Calif.), cover slipped and sealed. EMSA and supershift assays were performed essentially as described by Ortiz et al., 1996, supra. Oligonucleotides were synthesized by Life Technologies, Inc. (Gaithersburg, Md.) and purified by a polyacrylamide-urea gel. Oligonucleotides were end-labeled using [γ-$^{32}$P] ATP and T4 polynucleotide kinase. The following oligonucleotides were used:

A/B: AATTCGCTATTTTGGAAACTCCCCT-TAGGGGATGCCCCTCAACTGCG (SEQ ID NO:05)

A: AATTCGTTGCTATTTTGGAAACTCCCCTTG (SEQ ID NO:06)

B: AATTCGCTAGGGGATGCCCCTCAACTGCG (SEQ ID NO:07)

E: AATTCTTTGTGCAATTTCACTTATGATACCG (SEQ ID NO:08)

C: AATTCTCTAGATGAGAGAGCAGTGAGG-GAGAGACG (SEQ ID NO:09)

κB: AATTCGTCAGAGGGGACTTTCCGAGAG (SEQ ID NO: 10)

Anti-Sp1, anti-Sp3, anti-p65, and anti-c-rel were purchased from Santa Cruz Biotechnology (Santa Cruz, Calif.). Anti-p50, anti-p65, anti-α-actinin were from Upstate Biotechnology (Lake Placid, N.Y.). Anti-NPCP was from BAbCO (Berkeley, Calif.).

II. Results

A. Non-Rel Proteins Bind to the A/B site of the RANTES Promoter

The RANTES promoter has been subdivided into five regions (A–E) based upon deletion studies and reporter gene assays (Nelson et al., 1993 supra; Nelson et al., (1996) J. Immunol. 157, 1139–1148.; Ortiz et al., 1996 supra). The A site is very important for the promoter activity since point mutations or nonsense nucleotide replacement decreases the activity by 90% (Nelson et al., 1996 supra; Moriuchi et al., (1997) J. Immunol. 158, 3483–3491.). The A site binds both Rel and non-Rel proteins, with the non-Rel protein being upregulated in T cell nuclear extracts on day 3 after activation, coincident with RANTES message induction (Nelson et al., 1996, supra). The C site and E site also bind nuclear proteins that are strongly induced between days 3 and 5 after activation of normal peripheral blood T cells (Ortiz et al., 1996, supra).

In order to identify the non-Rel protein binding to the A site, Southwestern blotting was performed. Nuclear extracts from resting peripheral blood lymphocytes (PBL), Phytohemagglutinin (PHA) P activated PBL on different days, and other cell lines (i.e. AJY-CTL, "mature" T tumor line Hut 78, and B lymphoblastoid JY cells) were separated by SDS-PAGE and blotted on PVDF membranes. The membranes were hybridized with a radiolabeled oligonucleotide corresponding to the A/B region of the RANTES promoter and several nuclear proteins were detected. Proteins migrating at about 38 kDa, 75 kDa, and 105 kDa were detected in PBL only at late activation stages (days 3–7), showing kinetics similar to the factors detected by electrophoretic mobility shift assays (EMSA) (Nelson et al., 1996, supra). When an oligonucleotide containing three tandem A sites (A3) was used as the probe, the 38 kDa protein showed an even higher binding affinity.

B. Identification and Characterization of RFLAT-1

Figure 1:
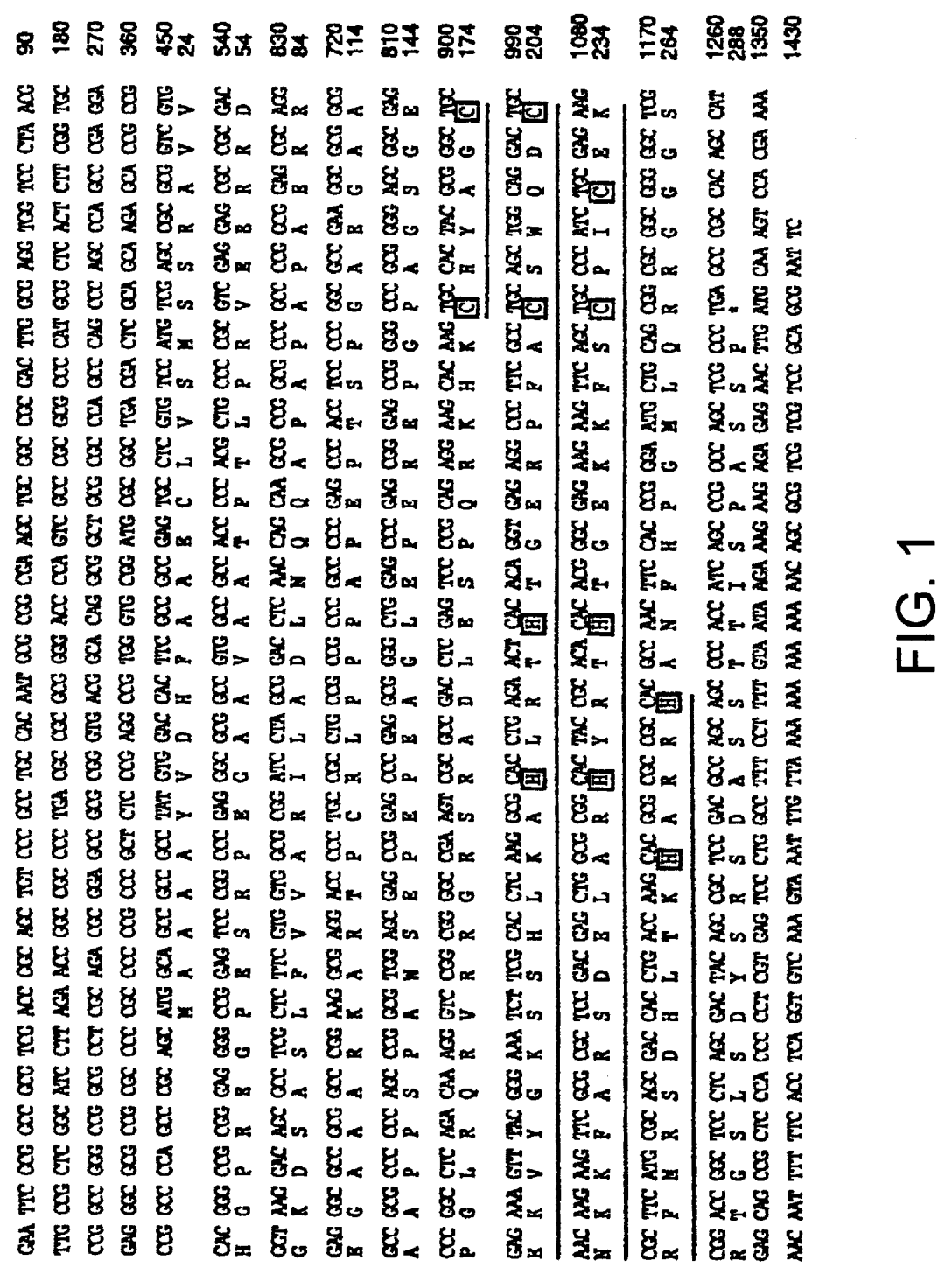

The results from the Southwestern analysis indicated that expression cloning could be used to identify proteins that bind to the A region of the RANTES promoter. A λgt11 cDNA library was constructed using poly(A)+ RNA from PBL on day 5 after activation by PHA, and the library was probed with radiolabeled A3 oligonucleotides. Upon screening, a cDNA clone (880 bp) was identified that contained three contiguous zinc fingers defined as a classical DNA binding motif (Mitchell and Tjian, (1989) Science 245, 371–378.). This clone was used to screen the original library to obtain a longer cDNA (1430 bp), which contains an open reading frame of 864 bp defined by a potential ATG start codon (nucleotide 379–381), a TGA stop codon (nucleotide 1243–1245), and is flanked by 378 (5') and 185 (3') untranslated nucleotide sequences (FIG. 1; SEQ ID NO:01)). The first methionine is surrounded by a consensus Kozak sequence (GCCCGCAGCATGG) (SEQ ID NO:03). A stop codon TGA is found 43 bp upstream in-frame with the start codon. This open reading frame encodes a 288 amino acid polypeptide with a calculated molecular mass of 31,680 daltons (FIG. 1; SEQ ID NO:02). A search of the Genbank database with the BLAST algorithm failed to identify any similar protein or cDNA sequence. Based on its function and expression, the factor has been named RFLAT-1 (for: RANTES Factor of Late Activated T Lymphocytes-1).

The deduced amino acid sequence contains three contiguous TFIIIA-like zinc-finger motifs at the C-terminus. This domain shows 73%, 72%, 65%, and 65% sequence similarity to those of Sp1 (Kadonaga et al., (1987) Cell 51, 1079–1090.), Sp3 (Kingsley and Winoto, (1992) Mol. Cell. Biol. 12,4251–4261), EKLF (Bieker, (1996) DNA Cell. Biol. 15:347–352), and BTEB (Sogawa et al., (1993) Nucleic Acids Res. 21, 1521–1532) proteins, respectively. Adjacent to the N-terminus of the zinc finger motif is a short sequence rich in basic amino acids, which does not show any obvious sequence homology to the consensus sequence for the basic domain of either Sp 1 family members or helix-loop-helix-leucine zipper proteins (Kadonaga et al., 1987, supra; Fisher et al., (1991) Genes Dev. 5, 2342–2352). Outside of these domains, the RFLAT-1 protein (1–145) is notably rich in proline (24/145), serine (10/145), and alanine (30/145) residues, which are known to constitute activation domains for a number of transcription factors (FIG. 2) (Mitchell and Tjian, 1989, supra).

To confirm that the 1430 bp cDNA clone encodes the full-length RFLAT-1 protein, the RFLAT-1 cDNA was subcloned into the pcDNA3.1 vector and subjected to in vitro transcription and translation. The reaction produced a doublet protein band with an apparent molecular mass of 38 kDa which was not present when the control vector was used, confirming the accuracy of the RFLAT-1 sequence. Alkaline phosphatase treatment converted the slower migrating band to the faster migrating form, indicating that the two bands are different forms of the protein, and that RFLAT-1 is likely to be phosphorylated. The phosphorylation of RFLAT-1 most likely accounts for its retarded migration on SDS-PAGE, causing the discrepancy between the predicted and the apparent molecular weight. To further confirm this, COS-7 cells were transfected with pcDNA3.1-RFLAT-1 and analyzed by Western blot for RFLAT-1 expression using polyclonal antibodies generated against recombinant RFLAT-1. Bands at approximately 38 kDa and lower were detected only in RFLAT-1 transfected cells, but not in empty vector transfected cells. Alkaline phosphatase treatment converted some, but not all, of the slower migrating species into the faster migrating form. These results confirm that the RFLAT-1 cDNA clone contains the entire coding region of the protein and also indicate that RFLAT-1 is phosphorylated.

C. Tissue and Cellular Distribution of RFLAT-1

Northern blot analysis was performed using poly(A)+ RNA from 16 different adult human tissues (PBL, colon (mucosal lining), small intestine, ovary, testis, prostate, thymus, spleen, pancreas, kidney, skeletal muscle, liver, lung, placenta, brain and heart). Two distinct transcripts (5 and 7.5 kb) were evident in all of the tissues analyzed, with the greatest abundance in PBL and thymus. RFLAT-1 expression was also assayed with poly(A)+ RNA from human cell lines of hematopoietic origin (i.e. PBL day5 (PHA), AJY, Hut78, Jurkat, JY, YT2C2, K562, Raji and Hela) and found to be widely expressed.

The intracellular localization of the RFLAT-1 protein was analyzed by immunofluorescence in COS-7 cells transiently transfected with RFLAT-1 cDNA. The overexpressed RFLAT-1 protein was primarily localized to the nuclear compartment of transfected COS-7 cells. RFLAT-1 staining was blocked specifically by addition of recombinant $His_6$-RFLAT-1. When cells were simultaneously stained with anti-RFLAT-1 and propidium iodide, RFLAT-1 and stained DNA colocalized in the nucleus. The combination of cellular fractionation and Western blotting also shows the primary localization of RFLAT-1 in the nucleus of activated T cells. For Jurkat, RFLAT-1 is only detected in the nucleus.

D. RFLAT-1 Binds DNA Sequences of the A Region of the RANTES Promoter

A carboxyl terminal portion of RFLAT-1, including the zinc finger DNA binding domain (nucleotides 550–1430), was isolated through expression cloning using an oligonucleotide probe containing three tandem A sites of the RANTES promoter. The same phage clones did not bind to the E or C site when a trimer E oligonucleotide or tetramer C oligonucleotide were used as probes. To further demonstrate its DNA binding specificity, the C-terminal portion of RFLAT-1 (amino acids 59–288) was expressed as a $His_6$-tagged recombinant protein and used for EMSA. Incubation of $His_6$-RFLAT-1 with the A/B probe revealed two retarded protein bands, suggesting that RFLAT-1 may bind to the A/B site by oligomerization. Binding activity was detected with the A probe, but not with the B probe. $His_6$-RFLAT-1 does not bind to the E or C probes in the assays, consistent with the results from the expression screening. Although the A/B site is very similar to the consensus sequence of the NF-κB binding site, and both the p50-p50 homodimer and p65-p50 heterodimer bind to the A/B region (Nelson et al., 1996 supra; Moriuchi et al., 1997 supra), $His_6$-RFLAT-1 did not bind to the κB oligonucleotide (FIG. 5A), which contains the consensus NF-κB recognition sequence derived from the immunoglobin promoter (Baeuerle and Henkel, (1994) Annu Rev Immuno. 12, 141–179).

To determine whether RFLAT-1 is present in the protein complex binding to the A/B region of the RANTES promoter which is induced upon T cell activation, nuclear extracts were isolated from resting and activated PBL for supershift assays. Two prominent bands were detected in the activated PBL nuclear extracts with the A/B probe; band 2 shows later kinetics than band 1. Addition of polyclonal anti-RFLAT-1 to the gel shift reaction mixture disrupted the complex formation for both band 1 and band 2, indicating that RFLAT-1 is indeed present in both complexes. Similar results were obtained when either the A or B probe was used (data not shown). The ability of the anti-RFLAT-1 polyclonal antiserum to disrupt the DNA-protein complex was not surprising since the antiserum was raised against the C-terminal portion of RFLAT-1 that contains the DNA-binding domain. Commercially available antibodies to other DNA binding proteins were also evaluated. Anti-p50, anti-p65, but not anti-c-rel, also supershifted both band 1 and band 2, demonstrating that NF-κB is also resent in both of the DNA-protein complexes. The same antibodies were used to test whether Sp1 or Sp3 are present in T cell A/B-protein complexes. Neither anti-Sp1 nor anti-Sp3 supershifted or disrupted the A/B DNA-protein complex, suggesting that Sp1 and its close family members are not involved in the upregulation of RANTES expression in activated T lymphocytes.

Nuclear extracts from other cell lines were also tested for A site binding. Both RFLAT-1 mRNA and protein are expressed in Jurkat, Hut78, JY and HeLa cells. Nuclear extracts from Hut78, a "mature" T cell tumor line which constitutively expresses low levels of RANTES, showed a similar A site binding pattern to that of nuclear extracts from PBL activated for 7 days with PHA. In contrast, nuclear extracts from Jurkat, JY, and HeLa, which do not express RANTES, did not show this pattern of binding to the A site.

E. RFLAT-1 is Expressed "Late" after T Cell Activation

RFLAT-1 is a component of the protein complex binding to the A/B region of the RANTES promoter. This complex is induced "late" (3–5 days) after T cell activation. To investigate these kinetics, total RNA from resting and activated PBL was isolated and RNA blots were probed with the 880 bp RFLAT-1 cDNA fragment (nucleotides 550–1430). Both transcripts (5 and 7.5 kb) were detected at comparable levels in resting and activated PBL. Therefore, during T cell activation, the RFLAT-1 steady-state mRNA level is constant. Nuclear extracts and cytoplasmic fractions were also isolated from quiescent and activated PBL for Western blot analysis. Proteins reactive with anti-RFLAT-1 antiserum migrating at 38 kDa and lower appeared in both PBL nuclear and cytoplasmic extracts only after day 3 of activation, indicating that the RFLAT-1 protein is expressed at the late activation stage of T lymphocytes. Western analysis was also performed for the NF-κB subunits p50 and p65. Both p50 and p65 proteins were enriched in the nucleus of activated T cells between day 3–5 after activation. In the cytoplasmic fractions, the protein levels of p50 and its precursor p105 steadily increased following cellular activation, but cytoplasmic p65 peaked at day 3 and then decreased. Conversely, nuclear p65 began to increase at day 5. These results show that the NF-κB protein is also increased at the late stage of T cell activation, and this increase is in part due to nuclear translocation.

F. RFLAT-1 Functions as a Transactivator for the RANTES Gene

To investigate the role of RFLAT-1 in the expression of RANTES, pcDNA3.1-RFLAT-1 was introduced into Jurkat T cells together with luciferase reporter constructs derived from the RANTES promoter. Cotransfection of RFLAT-1 with the pGL2-R-luciferase construct increased the promoter activity by ten-fold, demonstrating that RFLAT-1 can function as a transactivator for the RANTES promoter. A similar degree of induction was observed when a reporter gene construct containing only three A/B sites was used for the cotransfection, indicating that RFLAT-1 recognizes the A/B sequences. This was confirmed with pGL2-R-luciferase constructs in which either the A site, the B site, or both sites were replaced with nonsense oligonucleotides. Replacement of the A site decreased the induction more than replacement of the B site, indicating that the A site is more important than the B site in the RFLAT-1 mediated effect. When the C or E sites were disrupted, RFLAT-1 mediated induction was also impaired, indicating that these sites also play roles in transactivation. However, this decrease is most likely not mediated through direct binding to RFLAT-1.

To evaluate the role of RFLAT-1 in RANTES expression in non-T cells, RFLAT-1 cDNA and reporter gene constructs were introduced into NIH3T3 fibroblasts. RFLAT-1 also transactivated the RANTES promoter in fibroblasts, but the fold induction was only about half of that achieved in Jurkat T cells. In addition, only the A and B sites, but not the E and C sites, affected RFLAT-1-mediated RANTES induction in fibroblasts. This suggests that RFLAT-1 functions through different mechanisms in Jurkat T cells and in NIH3T3 fibroblasts.

To further investigate this possibility and to dissect the roles of RFLAT-1 and the NF-κB family members in RANTES gene induction in different cell types, the cDNA of the p65 subunit and the p50 subunit of the NF-κB protein were also subcloned into pcDNA3.1 and cotransfected into either Jurkat T cells or NIH3T3 fibroblasts for reporter gene assays. In T cells, both RFLAT-1 and p65 induced RANTES gene expression, but RFLAT-1 was a much more potent transactivator than p65, as shown by the greater degree of induction (ten fold versus three to four fold) when the same amount of plasmid was introduced (data not shown). When RFLAT-1, p65 and p50 were simultaneously overexpressed, a synergistic effect was observed. Identical cotransfection assays were performed in NIH3T3 fibroblasts. In this case, p65 played the dominant role in the transactivation of RANTES gene expression. p65 transactivation activity was so strong that it masked the effect of RFLAT-1 (40 fold induction by p65 alone versus 5 fold induction by RFLAT-1 alone). When all three cDNAs (RFLAT-1, p65, and p50) were overexpressed, RFLAT-1 enhanced the transcriptional induction by p65, but this effect was not synergistic. Thus, NF-κB is more potent than RFLAT-1 as a transactivator of RANTES gene expression in fibroblasts, while the reverse is true in T cells.

III. Further Characterization of RFLAT-1

A. Identification of Functional Domains of RFLAT-1.

RFLAT-1 belongs to the Kruppel-like transcription factor superfamily. Each member of this family members has a DNA-binding domain characterized by three TFIIIA-like zinc fingers residing on the C-terminus of the protein. However, little homology has been found outside of their DNA-binding domain. In addition, some of the proteins have distinct transactivation and repression domains. To identify transactivation domains for RFLAT-1, we fused fragments of RFLAT-1 cDNA to a yeast GAL4 protein DNA binding domain and created a series of GAL4-RFLAT-1 fusion proteins. The constructs encoding for these fusion proteins were cotransfected into fibroblasts with a GAL4 driven luciferase reporter gene. Results from these experiments showed that the N-terminus of RFLAT-1 contained most of the transactivation activity, and indicated that the minimum transactivation domain is amino acid 1–35. Further site-directed mutagenesis studies indicated that the acidic residues within this region are critical for its transactivation activity.

B. Cloning of Murine RFLAT-1 cDNA and Genomic Sequences.

The mouse RFLAT-1 cDNA was obtained by screening a murine activated spleen cDNA library. The sequence of a cDNA encoding murine RFLAT-1 is provided as SEQ ID NO: 11, infra. At the protein level, human and mouse RFLAT-1 share about 90% identity, indicating their important biological roles.

C. Identification of a Kinase that Phosphorylates RFLAT-1.

As shown above, the human RFLAT-1 protein is heavily phosphorylated. An array of kinases, including their expression and activities during T cell activation, were evaluated to identify which kinase is responsible for RFLAT-1 phosphorylation. A candidate: NILK, was identified. This kinase is only upregulated at the late stage of T cell activation, in agreement with upregulation of RFLAT-1 protein. Furthermore, the immunoprecipitated NILK from activated PBLs phosphorylates recombinant RFLAT-1. As controls, ERK1 kinase does not. These data indicate that NILK is a kinase that phosphorylates RFLAT-1.

D. Translational Control of RFLAT-1 During T Cell Activation.

RFLAT-1 protein is only induced at the "late" stage (3–5 days) of T cell activation. This pattern of expression is not regulated at the transcriptional level. Instead, experimental results indicate that the regulation is most likely at the translational level.

It is apparent from the above results and discussion that a novel transcription factor, RFLAT-1, as well as polypeptides related thereto and nucleic acid compositions encoding the same, are provided by the subject invention. These polypeptide and nucleic acid compositions find use in a variety of diverse applications, including diagnostic, screening and therapeutic applications. Also provided are novel methods of treating diseases associated with RANTES activity, including methods of treating inflammatory diseases, HIV, cancer and the like. Accordingly, the subject invention provides for a significant contribution to the field.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

What is claimed is:

1. A nucleic acid present in other than its natural environment, wherein said nucleic acid has a nucleotide sequence encoding RFLAT-1, and wherein said nucleic acid hybridizes under stringent hybridization conditions to a nucleic acid molecule having the sequence set forth in SEQ ID NO:1 or its complementary sequence.

2. A nucleic acid according to claim 1, wherein said nucleic acid has the nucleic acid sequence of SEQ ID NO:01.

3. A fragment consisting of at least about 20 contiguous nucleotides of the nucleic acid according to claim 1.

4. An expression cassette comprising a transcriptional initiation region functional in an expression host, a nucleic acid according to claim 1 under the transcriptional regulation of said transcriptional initiation region, and a transcriptional termination region functional in said expression host.

5. A host cell comprising an expression cassette according to claim 4 as part of an extrachromosomal element or integrated into the genome of a host cell as a result of introduction of said expression cassette into said host cell.

6. A nucleic acid according to claim 1, wherein said nucleic acid is a cDNA.

* * * * *